United States Patent
Lallemand et al.

(10) Patent No.: US 12,012,447 B2
(45) Date of Patent: Jun. 18, 2024

(54) COMPOSITIONS AND METHODS FOR REDUCING AT LEAST ONE SYMPTOM OF HUMAN ALLERGY TO CATS

(71) Applicant: Société des Produits Nestlé S.A., Vevey (CH)

(72) Inventors: Maud Isabelle Lallemand, Beauvais (FR); Ivan Filipi, St Louis, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 0 days.

(21) Appl. No.: 17/731,403

(22) Filed: Apr. 28, 2022

(65) Prior Publication Data

US 2022/0363739 A1    Nov. 17, 2022

Related U.S. Application Data

(60) Provisional application No. 63/189,450, filed on May 17, 2021.

(51) Int. Cl.
| | |
|---|---|
| *A61P 37/08* | (2006.01) |
| *A61K 47/42* | (2017.01) |
| *A61K 47/55* | (2017.01) |
| *C07K 16/18* | (2006.01) |

(52) U.S. Cl.
CPC .............. *C07K 16/18* (2013.01); *A61K 47/42* (2013.01); *A61K 47/551* (2017.08); *A61P 37/08* (2018.01)

(58) Field of Classification Search
CPC .. A61P 37/08; A61K 2039/505; A61K 39/395
See application file for complete search history.

(56) References Cited

U.S. PATENT DOCUMENTS

| | | | |
|---|---|---|---|
| 4,748,018 A | 5/1988 | Stolle et al. | |
| 5,080,895 A | 1/1992 | Tokoro | |
| 6,413,515 B1 | 6/2002 | Tsolkas et al. | |
| 8,454,953 B2 | 6/2013 | Wells et al. | |
| 11,641,842 B2 * | 5/2023 | Satyaraj | A01K 1/0052 424/130.1 |
| 2007/0098840 A1 * | 5/2007 | Axelrod | A23K 20/147 426/2 |
| 2010/0143266 A1 * | 6/2010 | Wells | A23K 20/10 424/171.1 |
| 2016/0324189 A1 * | 11/2016 | Callejon | A23K 50/40 |

FOREIGN PATENT DOCUMENTS

| | | | | |
|---|---|---|---|---|
| EP | 2763549 A1 * | 8/2014 | ............. | A23K 10/12 |
| WO | 2018138607 A1 | 8/2018 | | |

OTHER PUBLICATIONS

Satyaraj et al., "A Novel Approach to the Reduction of Cat Allergen Fel d1 Through Inclusion of an Egg Product Ingredient Containing Anti-Fel d1 IgY Antibodies in the Feline Diet", European Medical Journal Allergy Immunology, vol. 4, Issue No. 1, Jan. 1, 2019, pp. 40-46, XP055936097.

Satyaraj et al., "Reduction of Active Fel d1 from Cats Using an AntiFel d1 Egg IgY Antibody", Immunity, Inflammation and Disease, vol. 7, Issue No. 2, Mar. 9, 2019, pp. 68-73, XP055936106.

Satyaraj et a., "Anti-Fel d1 Immunoglobulin Y Antibody-containing Egg Ingredient Lowers Allergen Levels in Cat Saliva", Journal of Feline Medicine and Surgery, vol. 21, Issue No. 10, Oct. 28, 2019, pp. 875-881, XP055936112.

Steinberg, "The Curious History Behind a Biologic-Enriched Cat Food: Hyperimmune Avian IgY as a Means of Oral Adoptive Passive Immunization", Journal of Allergy and Clinical Immunology, vol. 148, Issue No. 6, Sep. 13, 2021, pp. 1473-1475, XP086885629.

"Purina Pro Plan LiveClear Voted Product of the Year 2021", Markets Insider, Feb. 18, 2021, pp. 1-6, XP002806942.

International Search Report and Written Opinion to PCT/IB2022/053957 dated Jun. 28, 2022.

\* cited by examiner

*Primary Examiner* — Robert T. Crow
*Assistant Examiner* — John P Nguyen

(57) ABSTRACT

The present application provides compositions, methods, and systems for reducing allergic response to Fel D1. Such compositions, methods, and systems generally include a supplement comprising an anti-Fel D1 molecule and an animal digest.

8 Claims, No Drawings

COMPOSITIONS AND METHODS FOR REDUCING AT LEAST ONE SYMPTOM OF HUMAN ALLERGY TO CATS

CROSS REFERENCE TO RELATED APPLICATIONS

This application claims the benefit of and priority to U.S. Provisional Application Ser. No. 63/189,450 filed May 17, 2021, the disclosure of which is incorporated in its entirety herein by this reference.

BACKGROUND

Approximately 20% of adults suffer from allergy to cats and/or their dander. Symptoms of cat allergies range from mild rhinitis and conjunctivitis to life-threatening asthmatic responses, and cat allergies are a major roadblock to cat ownership. For example, cat allergy is the primary reason given by cat owners for returning cats to animal shelters.

Most cat allergies are caused by a small stable glycoprotein called Fel D1 (*Feline domesticus* allergen number 1). This protein is transferred to cat dander by their grooming process and becomes airborne. Upon inhalation of cat dander having Fel D1 attached, an allergy cascade is triggered because of the recognition of the Fel D1 by human immune cells.

SUMMARY

The present disclosure is directed to supplements for reducing allergic response to Fel D1. Generally, the supplements can be fed to a cat with or without additional food compositions.

In one embodiment, a supplement for reducing allergic response to Fel D1 can comprise an anti-Fel D1 antibody and an animal digest.

In another embodiment, a method of making a supplement for reducing allergic response to Fel D1 can comprise admixing an anti-Fel D1 antibody and an animal digest.

In yet another embodiment, a system or kit for reducing allergic response to Fel D1 can comprise a food composition and a supplement, wherein the supplement comprises an anti-Fel D1 antibody and an animal digest.

In still another embodiment, a method of reducing symptoms of human allergy to a cat can comprise orally administering to the cat an effective amount of a supplement, wherein the supplement comprises an anti-Fel D1 antibody and an animal digest.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. The words "comprise," "comprises" and "comprising" are to be interpreted inclusively rather than exclusively. Likewise, the terms "include," "including" and "or" should all be construed to be inclusive, unless such a construction is clearly prohibited from the context. However, the devices disclosed herein may lack any element that is not specifically disclosed. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

Ranges are used herein in shorthand to avoid listing every value within the range. Any appropriate value within the range can be selected as the upper value or lower value of the range. Moreover, the numerical ranges herein include all integers, whole or fractions, within the range.

All percentages expressed herein are by weight of the total weight of the composition unless expressed otherwise. When reference is made to the pH, values correspond to pH measured at 25° C. with standard equipment. As used herein, "about" or "substantially" in reference to a number is understood to refer to numbers in a range of numerals, for example the range of −10% to +10%, −5% to +5%, −1% to +1%, or in one aspect, −0.1% to +0.1% of the referenced number.

The term "allergy" is synonymous with "allergic response" or "allergic reaction." Each of the terms refers to a state of immune responsiveness in an animal specific to an exogenous antigen (or "allergen") that is not otherwise harmful to the animal. A "symptom" of an allergic response refers to any measure of the immune responsiveness, e.g., on the molecular level (including measurement of an activity or expression of a protein, or transcript or gene), the cellular level, the organ level, the systemic level, or the organism level. Such symptoms can comprise one or more such levels. "Reducing at least one symptom" includes reducing such symptoms before they occur so that there are no symptoms to an allergic response and thus preventing the allergic response. In one aspect, the animal can be a human.

Symptoms may include generalized phenomena such as inflammation, respiratory complaints, swelling, or distress typically associated with allergy, rhinitis, edema, and allergic skin disorders including but not limited to atopic dermatitis (e.g., eczema), urticaria (e.g., hives) and angioedema, and allergic contact dermatitis. More specific phenomena that are "symptoms" of an allergic response include any measurable or observable change, for example at the cellular level, including but not limited to local or systemic changes in cell populations, eosinophilia, recruitment and/or activation of immune cells, including, for example, mast cells and/or basophils, changes in antigen-presenting cells (including but not limited to Fc∈RI-bearing dendritic cells), intracellular or molecular changes, including measurement or observations of one or more steps in an immunological cascade, release of intracellular compounds that mediate an allergic response (e.g., mediators), and changes in one or more cytokines (e.g., IL-3, IL-5, IL-9, IL-4, or IL-13) or related compounds or antagonists thereof. The skilled artisan will understand that certain symptoms as defined herein as more readily measured than others, and some are measured through subjective assessment or self-assessment of the symptom. For other symptoms, there are convenient or rapid assays or measurements for objectively assessing changes.

As used herein, an "effective amount" is an amount of any the compositions disclosed herein administered to a cat that reduces at least one symptom of cat allergy in a sensitized human in the same environment as the cat (e.g., a house, room, car, office, hotel, yard, garage). The relative term "reducing at least one symptom" and similar terms refer to a reduced severity resulting from the compositions and methods disclosed herein relative to the severity if the compositions and methods are not used but conditions are otherwise identical. As used herein, "reducing at least one symptom" includes, but is not limited to, reducing such symptoms before they occur so that there are no symptoms to an allergic response and thus preventing the allergic response.

The term "animal digest" means material which results from chemical and/or enzymatic hydrolysis of clean, undecomposed animal tissue. In certain embodiments, "animal digest" as used herein, is fully consistent with the definition of animal digest promulgated by the Association Of American Feed Control Officials, Inc. (AAFCO) as of Jan. 1, 2021. Generally, animal digests are fully consistent with the following description from the Food and Drug Administration (FDA), "with respect to flavors, pet foods often contain 'digests,' which are materials treated with heat, enzymes and/or acids to form concentrated natural flavors." Animal digest are generally derived from animal tissues, including cold-blooded marine animals, excluding hair, horns, teeth, hooves, and feathers. The skilled artisan will appreciate that while such excluded parts are not preferred, trace amounts might be found unavoidably even under good manufacturing practices. When an animal digest is dried, it is generally referred to as "dried animal digest." In one embodiment, the dried animal digest can exclude viscera. Animal digests in accordance herewith are suitable for use in food or feed compositions. Specifically included are (1) Digest of Beef (or Poultry, Pork, Lamb, Fish, etc.): material from beef (poultry, pork, etc.) which results from chemical and/or enzymatic hydrolysis of clean and undecomposed tissue; (2) Digest of Beef (or Pork, Lamb, etc.) By-Products: material from beef (poultry, pork, etc.) which results from chemical and/or enzymatic hydrolysis of clean and undecomposed tissue from non-rendered clean parts from cattle (pigs, lambs, fish, etc.), other than meat, for example lungs, spleen, kidneys, brain, livers, blood, bone, partially-defatted low-temperature fatty tissue, and stomachs and intestines, freed of their contents; and (3) Digest of Poultry By-Products: material which results from chemical and/or enzymatic hydrolysis of clean and undecomposed tissue from non-rendered clean parts of carcasses of slaughtered poultry such as heads, feet, and viscera. As used herein "poultry" encompasses any species or kind of bird, preferably chicken, turkey, duck, or other food species.

The terms "pet food," "pet food product" and "pet food composition" mean a product or composition that is intended for ingestion by a feline that provides at least one nutrient to the animal. Further in this regard, these terms mean that the product or composition is in a form ready for consumption and is not merely an intermediate from which a consumable product or composition is made, although other food compositions can be added in some embodiments, such as a supplement. The term "pet food" means any food composition intended to be consumed by a feline.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2021.

As used herein, an "anti-Fel D1 molecule" is any molecule able to specifically bind *Feline domesticus* allergen number 1 (Fel D1), for example an antibody, an aptamer, an agonist/antagonist of Fel D1, or portions of such molecules (e.g., an antigen binding fragment (Fab) of an antibody). The term "antibody" includes polyclonal and monoclonal antibodies of any type and from any species, as well as immunoglobulin fragments such as Fv, Fab, Fab', F(ab')2, or other antigen-binding antibody fragments, sequences or subsequences that interact with molecular specificity (e.g., demonstrate specific binding) with an antigen.

As used herein, "supplement" refers to any composition containing an anti-Fel D1 molecule and an animal digest including the use of the supplement with an existing pet food (e.g., to be mixed with or sprinkled on top of a main meal pet food) or the use of the supplement in the manufacturing of a pet food (e.g., as an ingredient in the basal or coating during the manufacturing of a pet food composition).

In one embodiment, the anti-Fel D1 molecule is an antibody (e.g., IgY) produced by immunizing an avian such as a chicken with Fel D1 to cause production of the antibody in eggs. The antibodies can be separated from the egg and administered to the animal; or the eggs and/or a part of the eggs such as the egg yolk can be applied directly onto or admixed with a food or other composition suitable for administration to an animal. In one aspect, the anti-Fel D1 molecule can be one of the embodiments of the molecules disclosed in U.S. Pat. No. 8,454,953 to Wells et al., "Methods for reducing allergies caused by environmental allergens," incorporated herein by reference in its entirety.

The term "long-term administration" means periods of repeated administration or consumption in excess of one month. Periods of longer than two, three, or four can be used for certain embodiments. Also, more extended periods that include longer than 5, 6, 7, 8, 9, or 10 months can be used. Periods in excess of 11 months or 1 year can also be used. Longer term use extending over 1, 2, 3, or more years can also be included in the invention. For certain animals, the animal will continue consuming on a regular basis for the remainder of its life. Sometimes this is referred to as consumption for "extended" periods.

The term "regular basis" of "regular administration" means at least monthly dosing with the compositions or consumption of the compositions, and in some aspects, weekly dosing. More frequent dosing or consumption, such as twice, three, or seven times weekly, can be used in certain embodiments. Still other embodiments include regimens that comprise at least once daily consumption. The skilled artisan will appreciate that the blood level of a compound or certain metabolites of that compound or which result after the consumption of that compound, may be a useful tool for assessing or determining dosing frequency. A frequency, regardless of whether expressly exemplified herein, that allows maintenance of a desired blood level of the measured compound within acceptable ranges is useful herein. The skilled artisan will appreciate that dosing frequency will be a function of the composition that is being consumed or administered, and some compositions may require more or less frequent administration to maintain a desired blood level of the measured compound.

The methods and devices and other advances disclosed herein are not limited to particular methodologies, protocols, and reagents because, as the skilled artisan will appreciate, they may vary. Further, the terminology used herein is for the purpose of describing particular embodiments only and does not limit the scope of that which is disclosed or claimed.

Unless defined otherwise, all technical and scientific terms, terms of art, and acronyms used herein have the meanings commonly understood by one of ordinary skill in the art in the field(s) of the present disclosure or in the field(s) where the term is used. Although any compositions, methods, articles of manufacture, or other means or materials similar or equivalent to those described herein can be used, specific devices, methods, articles of manufacture, or other means or materials are described herein.

EMBODIMENTS

The present disclosure relates generally to compositions and methods of using an active molecule that reduces at least one symptom of human allergy to cats. More specifically, the present disclosure is directed to enhancing the stability of the active molecule by incorporating the molecule with an animal digest.

In one embodiment, a supplement for reducing allergic response to Fel D1 can comprise an anti-Fel D1 molecule and an animal digest. Generally, the anti-Fel D1 molecule can be present in the supplement or the dried egg powder in amount of from about 0.0001% to about 1%. In various aspects, the anti-Fel D1 molecule can be present from about 0.0001%, 0.001%, or 0.01% to about 0.01%, 0.1%, 0.5%, or even 1%. Generally, the animal digest can be present in the supplement in an amount of from about 1% to about 90%. In various aspects, the animal digest can be present from about 1%, 10%, 20%, 30%, 40%, 50%, or 60% to about 30%, 40%, 50%, 60%, 70%, 80%, or even 90%.

The animal digest can be selected from the group consisting of poultry digests, pork digests, beef digests, sheep digests, lamb digests, fish digests, pork by-products digests, beef by-products digests, sheep by-products digests, lamb by-products digests, poultry by-products digests, fish by-products digests, more particularly in the group consisting of poultry digests, pork digests and fish digests, and combinations thereof. Suitable digests can include those available from Kemin Industries, Inc.; ADM Animal Nutrition; BASF SE; Cargill, Incorporated; Darling Ingredients Inc.; John Pointon & Sons Ltd.; DowDuPont Inc.; Omega Protein Corporation; Spécialités Pet Food SAS; AFB International; Proliver; and BHJ A/S. In one embodiment, the animal digest can be a dried animal digest.

In one embodiment, at least a portion of the molecule is specific for Fel D1. In another embodiment, at least a portion of the molecule comprises an antibody, an aptamer, or an agonist, or part of any of the foregoing, that binds specifically to Fel D1, in one embodiment comprising an antibody, or binding portion or fragment of an antibody, or other binding-specific protein or peptide, the antibody or other binding molecule is produced through biotechnological means, such as by large scale fermentation of a microorganism, through production in a readily obtained animal product, such as the milk or egg of an animal, or by production in a plant or crop (e.g., so-called "plantibodies"). In one embodiment, the anti-Fel D1 molecule can be a polyclonal antibody.

In a preferred embodiment, antibodies are produced by immunizing an avian such as a chicken with and antigent that causes production of the antibodies in eggs. The antibodies can be separated from the egg and administered to the animal or the eggs, or a part of the eggs such as the egg yolk, can be applied directly onto or admixed with a food or other composition suitable for administration to an animal. Methods for preparing antibodies using avian eggs and for administering avian eggs containing antibodies, particularly in food compositions, are well known to skilled artisans, e.g., U.S. Pat. Nos. 6,413,515, 5,080,895, 4,748,018, which are incorporated herein by this reference.

In a particular embodiment, antigens that cause eggs to produce anti-Fel D1 antibodies are used to immunize an avian, preferably a chicken; the avian eggs containing anti-Fel D1 antibodies are collected and optionally processed to enrich the concentration of the antibodies; the eggs or processed eggs are admixed with or applied to a food suitable for a cat; the food containing the antibodies is fed to the cat; and the antibodies complex with Fel D1 antigens in the mouth of the cat, thus neutralizing the antigenicity of the Fel D1 antigen and reducing or preventing allergies or their symptoms when an allergic animal comes into contact with the cat or the cat's environment, particularly objects that have been licked by or otherwise contacted by the cat in a manner that would leave Fel D1 allergens on the objects. As such, in one embodiment, dried egg yolk, alone or as part of a whole dried egg, can be the source of the anti-Fel D1 molecule.

In one embodiment, the anti-Fel D1 molecule can be present in the dried whole egg powder amount of from about 0.0001% to about 1%. In various aspects, the anti-Fel D1 molecule can be present from about 0.0001%, 0.001%, or 0.01% to about 0.01%, 0.1%, 0.5%, or even 1%. In one embodiment, the dried whole egg powder or any part thereof, can be present in the supplement from about 1% to about 99%. In various aspects, the dried whole egg powder or any part thereof, can be present from about 1%, 10%, 20%, 30%, 40%, 50%, or 60% to about 30%, 40%, 50%, 60%, 70%, 80%, or even 90%.

The supplements herein may further comprise substances such as minerals, vitamins, salts, antioxidants, nutrients, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium, and the like. Examples of vitamin useful herein include such fat-soluble vitamins as D and K, as well as B vitamins, vitamin E, vitamin C, vitamin A, etc. Inulin, amino acids, taurine, choline, enzymes, coenzymes, and the like may be useful to include in various embodiments. In one aspect, the additive can be selected from the group consisting of vitamin E, vitamin C, and mixtures thereof. Other components that can be added include carbohydrate or fiber sources, such as psyllium, cereal by-products, and malt; other components include course particles, anticaking agents, flowing agents. Other nutritional components can include yeasts, probiotics, and prebiotics.

In one embodiment, a method of making a supplement for reducing allergic response to Fel D1 can comprise admixing an anti-Fel D1 molecule and an animal digest. As discussed herein additives can also be admixed to form the supplement, in one step or separately.

In another embodiment, a system or kit for reducing allergic response to Fel D1 can comprise a food composition and a supplement, wherein the supplement comprises an anti-Fel D1 molecule and an animal digest. In one embodiment, the food composition can be a cat food. In one aspect, the cat food can be a complete and balanced cat food.

In such aspects, the kits suitable for reducing allergic response to Fel D1 can comprise in separate containers in a single package or in separate containers in a virtual package, as appropriate for the kit component, (a) a supplement comprising an anti-Fel D1 molecule and an animal digest; one or more of (b) one or more other ingredients suitable for consumption by an animal; optionally (c) instructions for how to combine or prepare the supplement and any other ingredients provided in the kit for administration to an animal; and optionally (d) instructions for how to use the combined kit components, prepared kit components, or other kit components for the benefit of an animal. The components can be each provided in separate containers in a single package or in mixtures of various components in different packages. The kits may comprise the ingredients in various combinations. For example, the kit could comprise a supplement in one container and one or more other ingredients in one or more other containers. Other such combinations can be produced by the skilled artisan based upon the characteristics of the ingredients and their physical and chemical properties and compatibilities.

In still another embodiment, a method for reducing allergic response to Fel D1 can comprise adding a supplement to a food composition, wherein the supplement comprises an anti-Fel D1 molecule and an animal digest; and administering the food composition to a cat. In one embodiment, the administration can be a regular administration. In another embodiment, the administration can be a long-term administration. In one aspect, the administration can be daily. In one embodiment, such administration can provide a dosing of about 0.1 mg to about 5 mg of the anti-Fel D1 molecule per day to the cat. In one aspect, the dosing can be about 0.2 mg to about 1 mg per day.

Yet another aspect of the present disclosure is a method of reducing symptoms of human allergy to a cat. The method comprises orally administering to the cat an effective amount of any of the supplements disclosed herein and/or supplements resulting from any of the methods disclosed herein. The supplements can be administered as part of a pet food further comprising at least one component selected from the group consisting of protein, fat, carbohydrate, vitamin, and mineral. The method can bind the anti-Fel D1 molecule to the Fel D1 in the cat's mouth and thereby prevent the Fel D1 from inducing an allergic reaction in a human susceptible to or suffering from an allergy caused by Fel D1.

EXAMPLES

By way of example and not limitation, the following non-limiting examples are illustrative of compositions and methods for reducing symptoms of allergy to cats in embodiments provided by the present disclosure.

Example 1—Production of Anti-Fel D1 Antibody

Chickens were inoculated with Fel d1 to induce the formation of anti-Fel d1-specific polyclonal immunoglobulin Y (sIgY) in the egg yolk. The eggs were collected, processed, and spray dried to form a whole egg yolk powder containing the sIgY.

Example 2—Production of Supplement

The powder of Example 1 was then combined with dried animal digest (thermally treated meat based enzymatic hydrolysate stabilized by drying), vitamin E (Vitamin E di-Alpha-Tocopheryl Acetate 50% Adsorbate), and vitamin C (Vitamin C Ascorbic Acid 35% Spray Dried) to form supplement #1 and combined with dried animal digest to form supplement #2 as described in Table 1.

TABLE 1

| Supplement | sIgY Powder (g) | Dried Animal Digest (g) | Vitamin E (g) | Vitamin C (g) |
|---|---|---|---|---|
| #1 | 0.32 | 1.583 | 3.7 | 1.2 |
| #2 | 0.185 | 0.815 | — | — |

Example 3—Stability Trial

The supplements of Example 2 were compared to the anti-Fel D1 antibody powder of Example 1 to determine stability according to various temperature profiles as described in Table 2.

TABLE 2

| Temp | Day | % Loss Powder from Example 1 | % Loss Supplement #1 from Example 2 | % Loss Supplement #2 from Example 2 |
|---|---|---|---|---|
| 140 F./60 C. | 0 | 0 | 0 | 0 |
| 140 F. | 3 | 44 | 25 | 28 |
| 140 F. | 7 | 58 | 43 | 43 |
| 140 F. | 10 | 60 | 50 | 48 |
| 140 F. | 14 | 66 | 45 | 58 |
| 140 F. | 17 | 69 | 58 | 56 |
| 120 F./49 C. | 0 | 0 | 0 | 0 |
| 120 F. | 3 | 23 | 5 | 8 |
| 120 F. | 7 | 28 | 7 | 17 |
| 120 F. | 10 | 30 | 25 | 22 |
| 120 F. | 14 | 49 | 18 | 27 |
| 120 F. | 17 | 44 | 26 | 29 |
| 120 F. | 21 | 53 | 37 | 36 |
| 120 F. | 24 | 50 | 26 | 40 |
| 120 F. | 28 | 53 | 34 | 40 |
| 120 F. | 35 | 53 | 35 | 49 |
| 120 F. | 42 | 45 | 31 | 44 |
| 120 F. | 56 | 48 | 39 | 56 |
| 100 F./38 C. | 0 | 0 | 0 | 0 |
| 100 F. | 14 | 26 | 12 | 13 |
| 100 F. | 28 | 27 | 12 | 14 |
| 100 F. | 42 | 24 | 27 | 6 |
| 100 F. | 56 | 30 | 21 | 19 |
| 100 F. | 70 | 31 | 27 | 20 |
| 100 F. | 84 | 35 | 17 | 33 |
| 100 F. | 98 | 40 | 32 | 25 |
| 100 F. | 112 | 32 | 20 | 33 |
| 100 F. | 126 | 42 | 36 | 26 |
| 100 F. | 140 | 39 | 36 | 25 |

As shown in Table 2, the supplements having dried animal digest were unexpectedly more stable evidenced by smaller percentage loss over time as compared to the control (sIgY powder from Example 1). At 140° F., after the first week, both supplements had a 15% improvement compared to the sIgY powder alone and after the second week, supplement #1 had a 21% improvement compared to the sIgY powder while supplement #2 had an 8% improvement. At 120° F., supplement #1 had improvements of 21%, 31%, 16%, 19%, and 18%, at 1 week, 2 weeks, 3 weeks, 4 weeks, and 5 weeks, respectively; while supplement #2 had improvements of 11%, 22%, 17%, 13%, and 4%, respectively, at 1 week, 2 weeks, 3 weeks, 4 weeks, and 5 weeks, respectively. At 100° F., supplement #1 had improvements of 14%, 15%, 9%, and 18% at 2 weeks, 4 weeks, 8 weeks, and 12 weeks, respectively; while supplement #2 had improvements of 13%, 13%, 11%, and 2%, at 2 weeks, 4 weeks, 8 weeks, and 12 weeks, respectively.

It should be understood that various changes and modifications to the presently embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A supplement for reducing allergic response to Fel D1, the supplement comprising dried egg yolk powder comprising an anti-Fel D1 molecule that is anti-Fel D1-specific polyclonal immunoglobulin Y (sIgY), the supplement further comprising a dried animal digest that is thermally-treated meat-based enzymatic hydrolysate,
   the dried egg yolk powder is about 1 wt. % to about 30 wt. % of the supplement,
   the anti-Fel D1 molecule is about 0.0001 wt. % to about 1 wt. % of the supplement, and
   the dried animal digest is about 20 wt. % to about 80 wt. % of the supplement.

2. The supplement of claim 1, further comprising an additive selected from the group consisting of vitamin E, vitamin C, and mixtures thereof.

3. A method of making a supplement for reducing allergic response to Fel D1, the method comprising:
   admixing (i) dried egg yolk powder comprising an anti-Fel D1 molecule that is anti-Fel D1-specific polyclonal immunoglobulin Y (sIgY) and (ii) a dried animal digest that is thermally-treated meat-based enzymatic hydrolysate, to form the supplement,
   the dried egg yolk powder is about 1 wt. % to about 30 wt. % of the supplement,
   the anti-Fel D1 molecule is about 0.0001 wt. % to about 1 wt. % of the supplement, and
   the dried animal digest is about 20 wt. % to about 80 wt. % of the supplement.

4. The method of claim 3, further comprising admixing an additive selected from the group consisting of vitamin E, vitamin C, and mixtures thereof.

5. A system for reducing allergic response to Fel D1, comprising:
   a food composition, and
   a supplement, wherein the supplement comprises dried egg yolk powder comprising an anti-Fel D1 molecule that is anti-Fel D1-specific polyclonal immunoglobulin Y (sIgY), the supplement further comprising a dried animal digest that is thermally-treated meat-based enzymatic hydrolysate, the dried egg yolk powder is about 1 wt. % to about 30 wt. % of the supplement, the anti-Fel D1 molecule is about 0.0001 wt. % to about 1 wt. % of the supplement, and the dried animal digest is about 20 wt. % to about 80 wt. % of the supplement.

6. The system of claim 5, wherein the food composition is a cat food.

7. A method for reducing allergic response to Fel D1, comprising:
   adding a supplement to a food composition, wherein the supplement comprises dried egg yolk powder comprising an anti-Fel D1 molecule that is anti-Fel D1-specific polyclonal immunoglobulin Y (sIgY), the supplement further comprising a dried animal digest that is thermally-treated meat-based enzymatic hydrolysate, the dried egg yolk powder is about 1 wt. % to about 30 wt. % of the supplement, the anti-Fel D1 molecule is about 0.0001 wt. % to about 1 wt. % of the supplement, the dried animal digest is about 20 wt. % to about 80 wt. % of the supplement; and
   administering the food composition to a cat.

8. The method of claim 7, wherein administration is a regular administration.

* * * * *